United States Patent [19]

Bradshaw et al.

[11] Patent Number: 5,002,543
[45] Date of Patent: Mar. 26, 1991

[54] STEERABLE INTRAMEDULLARY FRACTURE REDUCTION DEVICE

[76] Inventors: Anthony J. Bradshaw, 4760 Settles Point Rd., Suwanee, Ga. 30174; Michael E. Miller, 804 Edgewood Ave., Atlanta, Ga. 30307

[21] Appl. No.: 506,455
[22] Filed: Apr. 9, 1990
[51] Int. Cl.⁵ ............................................. A61F 5/04
[52] U.S. Cl. ...................................... 606/62; 606/95
[58] Field of Search ..................... 606/53, 59, 60, 102, 606/62-68, 104, 103, 95, 76-80, 144, 148, 150, 198; 604/105-110; 128/785, 786, 783, 784

[56] References Cited

U.S. PATENT DOCUMENTS

| | | | |
|---|---|---|---|
| 3,835,859 | 9/1974 | Roberts | 606/79 |
| 4,067,340 | 1/1978 | Lenoir | 606/79 |
| 4,474,177 | 10/1984 | Whiteside | 606/62 |
| 4,498,468 | 2/1985 | Hansson | 606/68 |
| 4,507,043 | 3/1985 | Flatau | 446/390 |
| 4,519,100 | 5/1985 | Wills | 606/63 |
| 4,632,101 | 12/1986 | Freedland | 606/68 |
| 4,644,951 | 2/1987 | Bays | 606/79 |
| 4,721,103 | 1/1988 | Freedland | 606/63 |
| 4,787,378 | 11/1988 | Sodhi | 606/67 |
| 4,791,919 | 12/1988 | Elloy | 606/62 |
| 4,913,164 | 4/1990 | Greene | 128/785 |

Primary Examiner—Robert A. Haffer
Assistant Examiner—Michael Brown
Attorney, Agent, or Firm—Thomas & Kerr

[57] ABSTRACT

A steerable intramedullary fracture reduction device has an elongated shaft with a steerable tip pivotally mounted to the distal end of the shaft. Tip actuating apparatus near the proximal end of the shaft enable the operator to steer the tip and the shaft into successive segments of the fractured bone, even when the segments are transversely or rotationally displaced so that the segments can be aligned by the shaft.

19 Claims, 3 Drawing Sheets

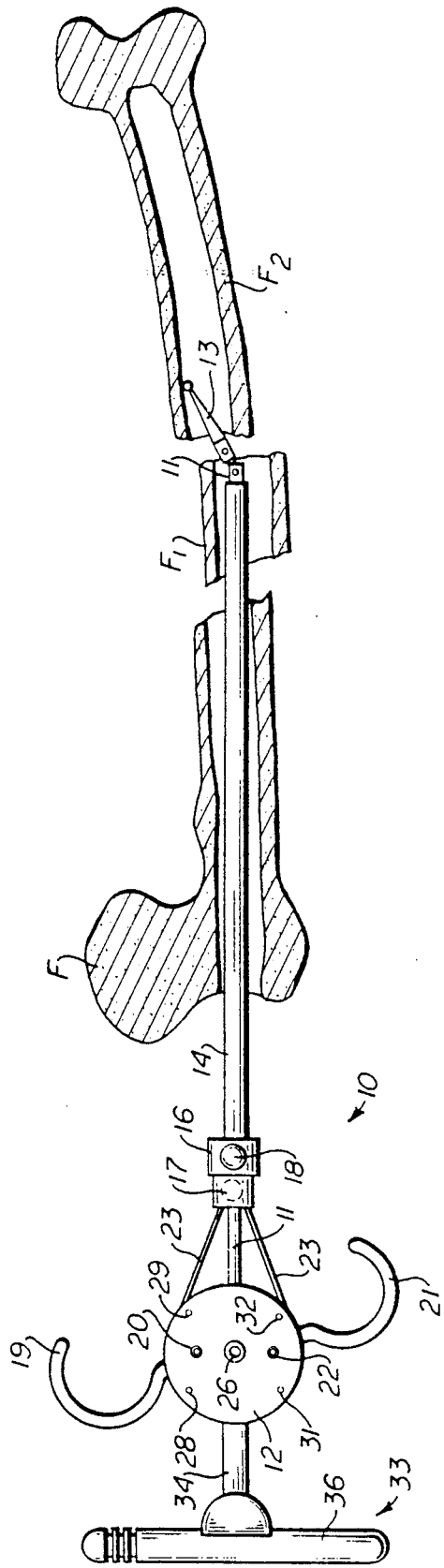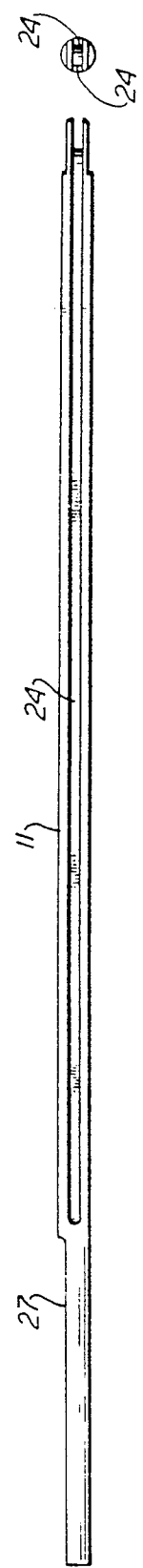
FIG. 1
FIG. 2

STEERABLE INTRAMEDULLARY FRACTURE REDUCTION DEVICE

BACKGROUND OF THE INVENTION

This invention relates to orthopedic tools, and, more particularly, to a steerable intramedullary fracture reduction device for use in reducing fractures in long bones in the body.

Severely comminuted fractures often exhibit bone fragments or irregular sections of bone which are displaced either axially, rotationally, or both from the main portion of the bone. In order that the fracture may be reduced, an intramedullary nail such as that shown in copending U.S. patent application Ser. No. 07/445,376, filed Dec. 4, 1989, now U.S. Pat. No. 4,946,459, issued Aug. 7, 1990, is inserted into the interior of the bone in the bone channel, and the fragments or sections of bone pulled together. Where there is lateral or rotational displacement of the bone sections, however, it is often difficult to align and rotationally move the bone sections with the nail itself. Current realignment procedures involve insertion of a wire into the medullary canal of, for example, the femur, from the proximal end thereof, which is then guided through the bone segments, often in conjunction with a partially inserted nail, for leverage. When the segments are aligned, the nail is fully inserted and the wire withdrawn. Such an arrangement does not readily accomplish rotational alignment, and, especially in cases of severe lateral displacement, requires a great deal of probing to pass the wire into a misaligned bone segment. In addition, muscle tissue attached to the displaced bone segments tends to hold the segments in their displaced position, and often the guide wire is not sufficiently rigid to overcome the muscle force, thereby necessitating further insertion of the nail.

An example of an apparatus for reducing fractures of small bones is shown in U.S. Pat. No. 4,622,960 of Tam wherein wires are used to pull the bones together. This apparatus is primarily used for manipulating the wire, not the bone, and requires that holes be drilled in the bone. An apparatus for manipulating and suturing cartilage is shown in U.S. Pat. No. 4,741,330 of Hayhurst, and is useful primarily for arthroscopic surgery, not for reducing bone fractures.

SUMMARY OF THE INVENTION

The present invention, in a preferred embodiment thereof, comprises a substantially rigid elongated nail guide fracture reducing device having a cable controlled movable tip which is designed to be inserted into the medullary canal of, for example, the femur, at the nail entry point in the proximal end of the bone, and steered into the successive bone segments.

The device of the invention comprises a first elongated, rigid shaft having diametrically opposed grooves extending over a substantial portion of the length thereof to what, in practice, is the distal tip. The other or proximal end of the shaft has a flat machined thereon. The distal tip of the shaft is rounded on one side and flat on the other. Pivotally mounted to the distal tip is steerable tip of substantially conical shape and having an enlarged head at the end thereof with the base of the tip bearing against the flat of the tip of the shaft. A continuous tip actuating cable is contained in the grooves and extends to the distal end of the shaft where it is fixedly connected to the pivotally mounted base of the steerable tip. The slotted shaft is inserted into an elongated intramedullary tube or sleeve which in turn is releasably affixed to the shaft by means of a tube collar.

The proximal ends of the cable are affixed to a pair of finger triggers which are pivotally mounted on opposite sides of a mounting member affixed to the shaft and which control the tip actuation by the cable. A handle stem and T-handle are affixed to the mounting member. An operator actuates the cable, thus pivoting the steerable tip, by pulling on the appropriate finger trigger, with the T-handle bearing against the palm of his hand. The flat on the end of the shaft tip against which the base of the movable tip rests provides a reference position for the operator, from which the tip can be moved from a neutral or aligned position in one direction but not the other.

In practice, the nail guide is inserted into the medullary canal at the nail entry point at the proximal end of the femur, for example. It is then forced directly through the bone marrow, with the movable tip being used to steer it into the next bone segment and the process is continued until it has passed through all of the bone segments. Because of its rigidity, the guide can be manipulated to align each segment with the preceding one, until all segments are aligned. Where a segment is rotationally displaced, the tip is forced into it and angled with respect to the shaft and sleeve within the canal, thereby gripping the bone segment in its interior with sufficient force to permit rotation of the segment by rotation of the device. In this way the various segments are aligned both rotationally and laterally. The tube is then loosened from the shaft and the shaft and tip withdrawn, leaving the tube within the medullary canal to serve as a guide for insertion of, for example, a reaming guide wire. The reduction of the fracture is thus completed by removal of the tube and insertion of the nail, as disclosed in the aforementioned U.S. Pat. No. 4,946,459.

The various features and advantages of the present invention will be more readily apparent from the following detailed description, read in conjunction with the accompanying drawings.

BRIEF DESCRIPTION OF THE DRAWINGS

FIG. 1 is a view of the device of the present invention in operation on a fractured femur;

FIG. 2 is a side view of an element of the device of FIG. 1;

DETAILED DESCRIPTION OF THE DRAWINGS

Figure 3:
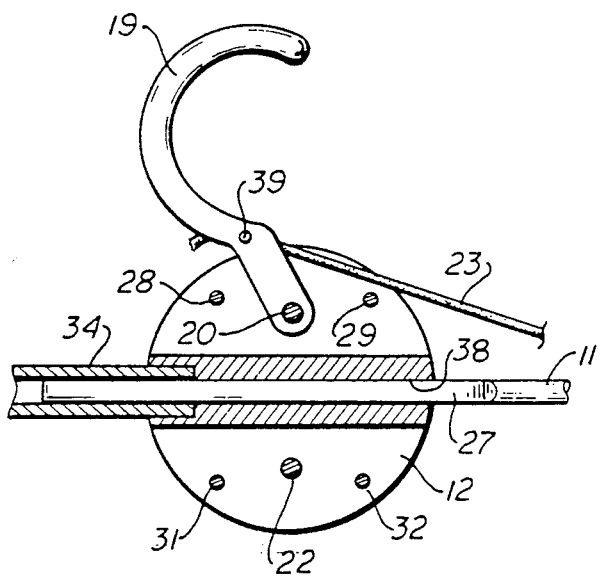
FIG. 3 is a partial cross-sectional view of the trigger mounting arrangement of the device of FIG. 1.

In FIG. 1 there is shown the device 10 in a preferred embodiment of the present invention as used, for example, in the alignment of bone fragments in a fractured femur, designated F. Device 10 comprises a shaft 11, which extends from a trigger mounting member 12 near the proximal end of the device to a movable tip 13 pivotally mounted to the distal end of the shaft 11. Carried on shaft 11 is an elongated sleeve 14 which is affixed to shaft 11 by means of a collar 16 which is affixed to shaft 11 by a locking screw 17, shown in dotted outline, and is affixed to sleeve 14 by locking screw 18.

Pivotally mounted in trigger mounting member 12 by means of pivot pins 20 and 22 are first and second triggers 19 and 21, to which are affixed the ends of a cable 23. Cable 23 extends from the triggers 19 and 21 along the length of the device in grooves 24, best seen in FIG. 2, cut in shaft 11, being affixed to tip 13 at the distal end of shaft 11. The details of the connection of cable 23 to the triggers 19 and 21 and to the tip 13 will be discussed more fully hereinafter. Trigger mounting member 12 is affixed to shaft 11 by means of a set screw 26 bearing against a flat 27 on shaft 11 as best seen in FIG. 2. 28, 29, 31 and 32 which serve to limit the travel of triggers 19 and 21 as will be explained more fully hereinafter. Mounted on member 12, as, for example, by welding, or by a press fit, is a T handle 33 comprising a shaft 34 and a cross piece 36.

As can be seen in FIG. 1, the device is inserted into the intramedullary channel of the bone through a previously drilled hole for ultimate insertion of the intramedullary nail. The steerable tip 13 allows the operator to steer device 10 into and through broken sections of bone such as $F_1$ and $F_2$ and, by manipulation of device 10, these sections can be aligned longitudinally. Even relatively severe transverse displacement of bone sections can thus be aligned, due to the ability of steerable tip 13 to be pivoted through an angle greater than 90 degrees, as will be discussed in connection with FIGS. 5a and 5b, and further due to the rigidity of the device 10.

Figure 4:
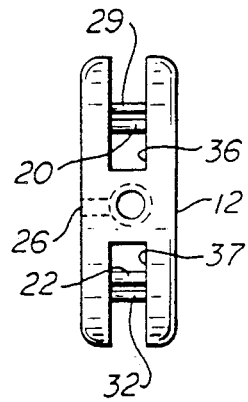
FIG. 4 is an end view of the trigger mounting member of FIG. 3.

In FIGS. 3 and 4, the details of trigger mounting member 12, and the mounting thereof on shaft 11 are shown. For clarity, only one trigger 19 and one end of cable 23 have been shown, it being understood that trigger 21 and the other end of cable 23 are mounted in the same way. Trigger mounting member 12 is generally, although not necessarily, circular in shape, and preferably made of a non-toxic, non-reactive material such as stainless steel, as are the remaining components of device 10, for example. First and second slots 36 and 37 are cut in member 12 to accommodate and allow free movement of triggers 19 and 21, which are pivotally mounted on pins 20 and 22 respectively. A bore 38 extends through member 12 which accommodates shaft 11, and member 12 is affixed to shaft 11 by set screw 26 bearing against flat 27 on shaft II. As can be seen in FIG. 3, shaft 11 extends through member 12, thus allowing for some length adjustment of the apparatus 10, depending on the length of bone to be operated on. Shaft 34 of T handle 33 is hollow to allow longitudinal movement of shaft 11. Shaft 34 can be a press fit in member 12, or it may be welded thereto or fastened in any suitable way to be rigidly affixed to member 12.

The end of cable 23 is pinned by a pin 39, or otherwise fastened to trigger 19, and in the same manner, the other end of cable 23 is affixed to trigger 21. Stop pins 28 and 29 are positioned to limit the travel of trigger 19, as are pins 31 and 32 for limiting travel of trigger 21. Pins 28 and 29, and 31 and 32, are necessary to prevent excess movement of pivotally mounted tip 13, which excess might damage the apparatus 10. Inasmuch as the operator cannot see the position of tip 13, without the stop pins, he could accidentally move tip 13 beyond its allowable range and thereby damage the tip mounting and connection to cable 23.

Figure 5A:
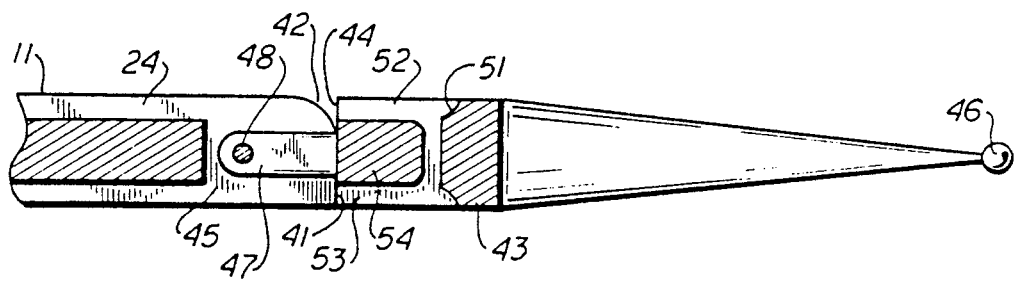
FIGS. 5a and 5b are side elevation view and a plan view of a preferred movable tip mounting arrangement of the device of FIG. 1.
Figure 5B:
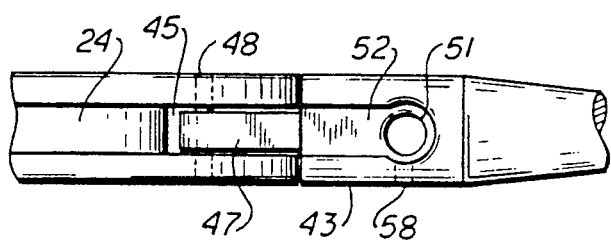

FIGS. 5a and 5b depict the details of a preferred arrangement for mounting the pivotal tip 13 to the rod 11. as can be seen, the end of rod 11 has a flat portion 41 and a rounded portion 42. Tip 13 has a base 43 with a flat end surface 44 that is adapted to bear against flat portion 41 when the tip 13 is in its neutral, or aligned position. The other end of tip 13 terminates in a ball 46 which facilitates movement of tip 13 through the bone section and prevents snagging. Extending from the base 43 is a tang 47 having a hole in its end through which a pivot pin 48 extends. The end of shaft 11 has a slot 45 cut therein to receive tang 47 so that it may pivot on pin 48. Actuating cable 23 is connected to tip 13 as follows. A countersunk hole 51 is drilled through base 43 and slots 52 and 53 join hole 51 to the bottom surface 44, thus forming a bearing portion 54 within base 43. That end of portion 54 adjoining the hole 51 is supplied with rounded edges 56 and 57. Cable 23 is passed through slot 52, around the end of portion 54, and through slot 53, as best seen in FIG. 6b. A set screw 58 is threaded into base 43 and bears against cable 23, locking it in place.

With the arrangement of FIGS. 5a and 5b, it can be seen that actuation of the triggers 19 and 21 can cause tip 13 to swing through greater than 90 degrees in one direction, as shown in dashed outline, but, because of the flat surface 44 bearing against flat surface 41, tip 13 cannot be pivoted in the other direction past the neutral or straight ahead alignment. This arrangement enables the operator to know, with a fair degree of accuracy, the location of the tip, i.e., its position relative to the neutral position, at all times.

It is to be understood that the arrangement of FIGS. 5a and 5b represents a preferred embodiment, however, persons skilled in the art might readily create alternative arrangements to accomplish the same end without departing from the scope of the present invention.

Figure 6A:
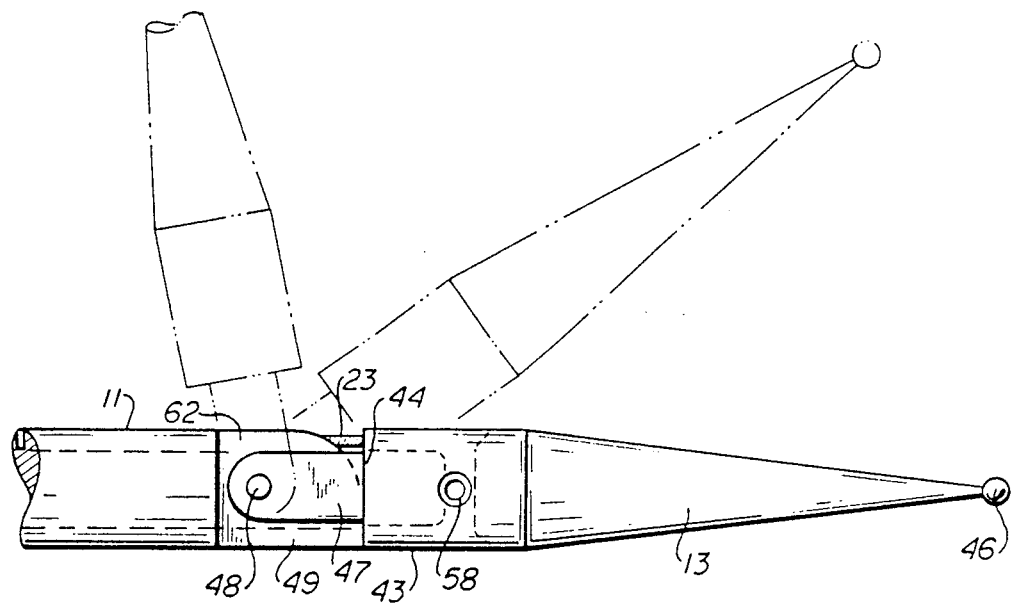
FIGS. 6a and 6b are side elevation views of an alternative tip mounting arrangement; and, FIG. 7 is a detail view of the manner in which the device of FIG. 1 rotates a bone segment.
Figure 6B:
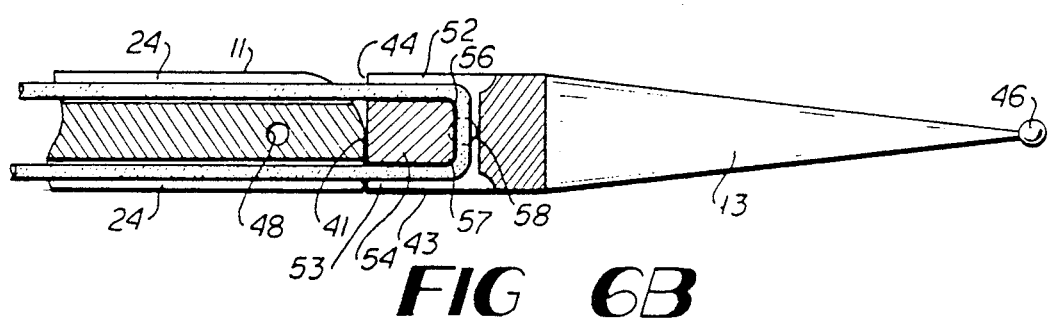

One such alternative arrangement is depicted in FIGS. 6a and 6b, wherein the parts that are the same in FIGS. 5a and 5b bear the same reference numerals. In the arrangement of FIGS. 6a and 6b, base portion 43 has two tangs extending therefrom, only one of which, tang 61, is shown. The end of shaft 11 is recessed by flats cut on either side, only flat 62 being shown, and the two tangs straddle the flats. Pin 48 extends from tang 61 through shaft 11 and into a hole in the matching tang (not shown) extending from base 43. With such an arrangement, the tangs do not project beyond the surface of shaft II, so that sleeve 14 may be slid over tip 13 when the tip is in a neutral or aligned position.

Figure 7:
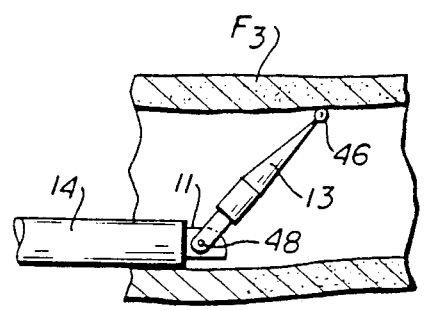

Thus far the discussion has been primarily directed to the alleviation and reduction of transverse or lateral bone displacements. In FIG. 7 there is shown the device of the present invention as used to relieve rotationally displaced bone segments. The steerable tip 13 is directed into the bone segment, designated $F_3$ a sufficient distance so that sleeve 14 also enters the medullary canal of the segment. Tip 13 is then pivoted so that ball 46 bears against the interior wall of the bone segment. Tip 13 is pivoted still further so that sleeve 14 is forced down and bears against the interior wall of the segment 180 degrees removed from ball 46. When a constant pulling force is maintained on the appropriate trigger member 19 or 21, the device is wedged tightly within the bone, and the bone can then be rotated by rotation of T handle 33 until proper rotational positioning is achieved.

OPERATION

In operation, the device 10 is inserted through a previously drilled hole in the top of the bone, as seen in FIG. 1, and the various bone segments aligned both transversely and rotationally, as discussed hereinbefore. When all of the fracture area has been passed through by the device, sleeve 14 is loosened from shaft 11, and the device 10 is withdrawn, leaving the sleeve 14 in place within the bone. A reaming guide wire, not shown, is then passed through the sleeve 14 and sleeve 14 is then removed. From this point on, regular nailing procedures, as discussed in the aforementioned U.S. Pat. No. 4,946,459, can be followed.

From the foregoing it can be seen that the device of the present invention, a preferred embodiment of which has been shown, is a novel and efficient fracture reducing device and functions to align fracture bone segments to facilitate insertion of reaming wires and intramedullary nails into the bone after the fracture segments have been aligned. While the device has been shown as used with a femur, other bones, both long and short, may be treated by an appropriately scaled version of that herein illustrated.

It will be apparent that various and numerous modifications of the device may occur to workers in the art without departure from the spirit and scope of the invention.

We claim:

1. An intramedullary fracture reduction device comprising
    an elongated shaft having distal and proximal ends, and a longitudinal axis,
    means for steering the distal end of said shaft into displaced bone segments, said means comprising,
    a movable tip pivotally mounted to the distal end of said shaft and extending beyond said distal end, said tip having a neutral position substantially coaxial with and extending beyond said shaft.
    tip actuating means for causing said tip to pivot through a range of operative positions relative to said shaft, and
    control means for controlling said tip actuating means, said control means being positioned adjacent said proximal and of said shaft.

2. An intramedullary fracture reduction device as claimed in claim 1 wherein said tip actuating means comprises a cable extending along the length of said shaft on opposite sides thereof.

3. An intramedullary fracture reduction device as claimed in claim 2 wherein said cable is affixed to one end of said movable tip.

4. An intramedullary fracture reduction device as claimed in claim 2 wherein said elongated shaft has first and second grooves along at least a portion of the length thereof in which said cable is carried.

5. An intramedullary fracture reduction device as claimed in claim 2 wherein said movable tip has a base portion having a flat end surface adapted to bear against the distal end of said shaft.

6. An intramedullary fracture reduction device as claimed in claim 5 wherein said distal end of said shaft has a rounded portion and a flat portion, said flat end surface being adapted to bear against said flat portion when the movable tip is aligned with said shaft.

7. An intramedullary fracture reduction device as claimed in claim 6 wherein said base portion has a bore therein for passage of said cable, said hole being connected to said flat end surface by first and second slots adapted to contain said cable.

8. An intramedullary fracture reduction device as claimed in claim 7 and further including means for fixing said cable in said bore.

9. An intramedullary fracture reduction device as claimed in claim 2 wherein said control means comprises a trigger mounting member affixed to said shaft, said trigger mounting member having first and second actuating triggers pivotally mounted thereto, said cable having a first end connected to said first trigger and a second end connected to said second trigger.

10. An intramedullary fracture reduction device as claimed in claim 9 and further including means in said trigger mounting member for limiting the pivoting movement of said triggers.

11. An intramedullary fracture reduction device comprising
    an elongated rigid shaft having a distal end and a proximal end and a longitudinal axis,
    a steerable tip pivotally mounted at and extending beyond the distal end of said shaft, said steerable tip having a neutral position aligned with said shaft coaxially therewith,
    means for causing said steerable tip to pivot relative to said shaft through a range of positions from the neutral position to a position of at least ninety degrees to the longitudinally axis, said means including a control assembly adjacent the proximal end of said shaft,
    a handle mounted to said control assembly, and
    a sleeve member carried by said shaft and adapted to slide over said shaft and said steerable tip when said tip is in the neutral position.

12. A intramedullary fracture reduction device as claimed in claim 11 wherein said steerable tip has a base having a flat end surface, and a first tang extending from said end surface toward said shaft, said first tang having a transverse hole therein.

13. An intramedullary fracture reduction device as claimed in claim 12 wherein the distal end of said shaft has a slot cut therein for receiving said first tang.

14. An intramedullary fracture reduction device as claimed in claim 13 wherein said distal end of said shaft has a transverse hole therein, and a pivot pin extending through said transverse hole and the transverse hole in said first tang.

15. An intramedullary fracture reduction device as claimed in claim 12 and further including a second tang extending from said end surface and spaced from said first tang, said second tang having a transverse hole therein aligned with the transverse hole in said first tang.

16. An intramedullary fracture reduction device as claimed in claim 15 wherein the distal end of said shaft has first and second opposed flats thereon, said first and second tangs being adapted to straddle the end of said shaft at said flats.

17. An intramedullary fracture reduction device as claimed in claim 16 wherein said shaft has a transverse hole therein extending between said flats, and a pivot pin extending through the transverse hole in said first tang, the transverse hole in said shaft, and the transverse hole in said second tang.

18. A method of reducing fracture in a bone, wherein the bone has distal and proximal ends and a hole drilled in the proximal end communicating with the medullary canal of the bone, the method comprising the steps of inserting an elongated steerable intramedullary fracture reducing device through the hole in the bone into the medullary canal, the device having a steerable tip at its distal end and an elongated sleeve member, steering the device by means of the steerable tip through fracture bone segments and manipulating the device to align the segments, loosening the sleeve from the device and withdrawing the device, leaving the sleeve in the medullary canals of the aligned bone segments.

19. The method as claimed in claim 18 and further including the steps of insertinq the tip and a portion of the sleeve into the medullary canal of a bone segment that has been rotationally displaced, actuating the tip to cause it to bear against the inner wall of the bone, at one point, continuing actuating the tip until the sleeve bears against the inner wall of the bone in an area on the other side of the inner wall from the point where the tip bears against the bone, rotating the device to rotate the rotationally displaced bone segment, and aligning the rotated bone segment with the remainder of the bone.

* * * * *